United States Patent [19]

Donaldson

[11] Patent Number: 5,550,601
[45] Date of Patent: Aug. 27, 1996

[54] METHOD AND APPARATUS FOR OCULAR MOTILITY TESTING

[76] Inventor: William B. M. Donaldson, 45 Carlton Pl., Aberdeen AB2 4BR, Scotland

[21] Appl. No.: 313,051
[22] PCT Filed: Apr. 5, 1993
[86] PCT No.: PCT/GB93/00715
 § 371 Date: Sep. 30, 1994
 § 102(e) Date: Sep. 30, 1994
[87] PCT Pub. No.: WO93/19661
 PCT Pub. Date: Oct. 14, 1993

[30] Foreign Application Priority Data

Apr. 3, 1992 [GB] United Kingdom ............... 9207315

[51] Int. Cl.⁶ .................................................. A61B 3/14
[52] U.S. Cl. ........................ 351/209; 351/205; 351/246
[58] Field of Search ................................... 351/209, 210, 351/211, 206, 205, 246, 245, 221

[56] References Cited

U.S. PATENT DOCUMENTS 5,070,883 12/1991 Kasahara ................................. 351/209

5,094,521 3/1992 Jolson et al. ............................ 351/210

*Primary Examiner*—William L. Sikes
*Assistant Examiner*—Hung Xuan Dang
*Attorney, Agent, or Firm*—Woodcock Washburn Kurtz Mackiewicz & Norris

[57] ABSTRACT

An apparatus for ocular motility testing comprising, head positioning means for location of the head of a patient in a predetermined position, gaze-detecting means adapted to image both eyes simultaneously with the patient's head in a predetermined position while the patient's eye(s) follow a target on a screen, and computing means for computing the position of visual axis of the eyes with reference to a primary position, and store means associated with a target display means and the computing means to store the positions of the target and the positions of the visual axes; characterized in that the gaze-detecting means is disposed adjacent the eyes of the patient and comprises left and right gaze direction detecting means acting independently, the gaze-detecting means including gaze occluder means operable selectively to occlude a patient's eye relative to the target, without obstructing the gaze detecting means.

8 Claims, 1 Drawing Sheet

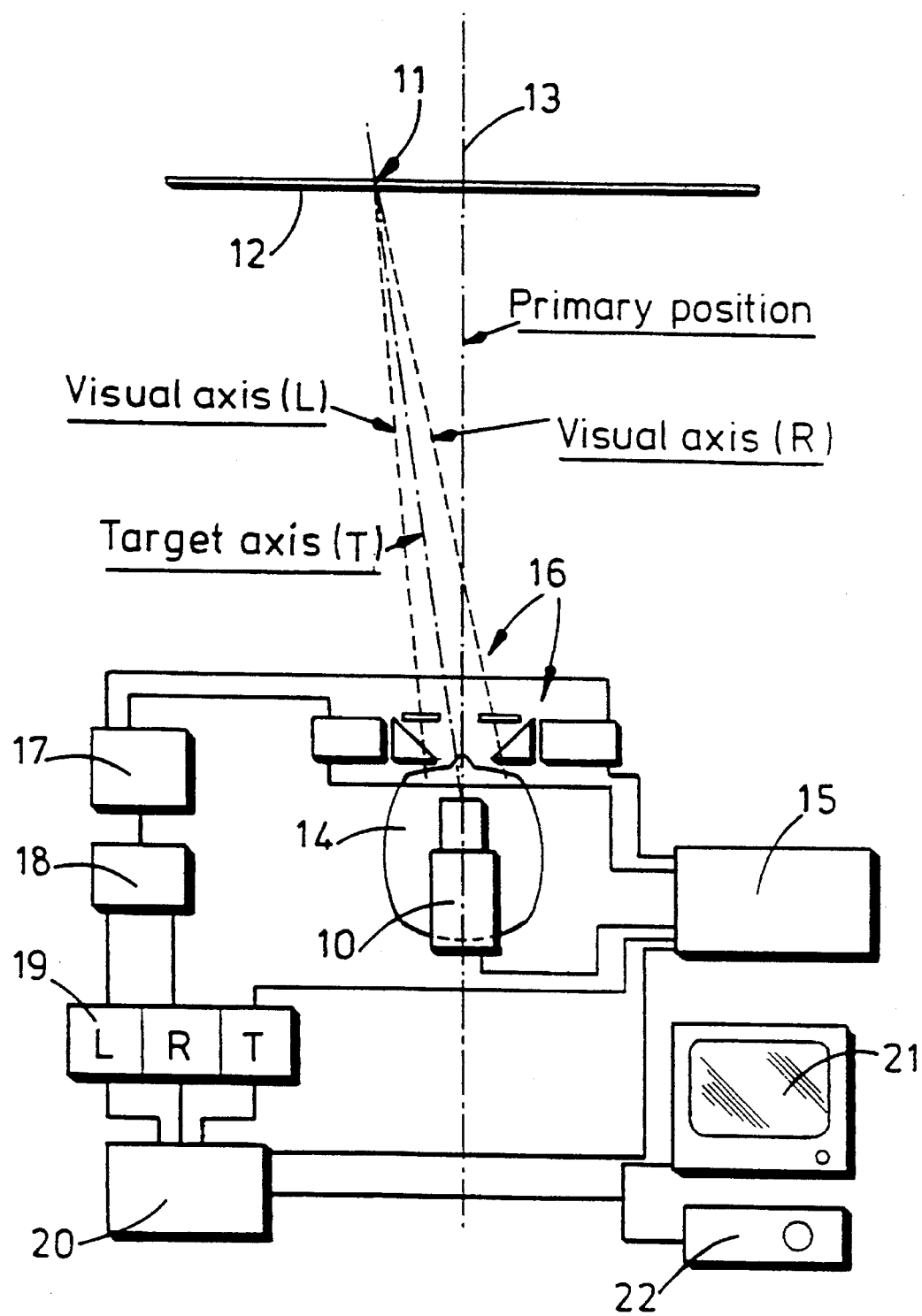

METHOD AND APPARATUS FOR OCULAR MOTILITY TESTING

This invention relates to a method of, and to apparatus for use in ocular motility testing.

U.S. Pat. No. 5,094,521 reveals an apparatus for ocular motility testing comprising head positioning means for location of the head of a patient in a predetermined position, gaze-detecting means adapted to image both eyes simultaneously with the patient's head in a predetermined position while the patients eye(s) follow a target on a screen, and computing means for computing the position of visual axis of said eyes with reference to a primary position, and store means associated with target display means and said computing means to store the positions of the target and the positions of the visual axis.

The present invention is characterised in that the gaze-detecting means is disposed adjacent the eyes of the patient and comprises left and right gaze direction detecting means acting independently.

In the inventive embodiment in accordance to the present invention the gaze-detecting means is disposed close to the eyes of the patient and comprises mutually independent left and right gaze direction detectors. The gaze-detecting means may also include gaze occluder means operable selectively to occlude a patient's eye relative to the target. The arrangement of the invention may include control means programmable to drive the projection means so that the target is either displayed at different positions or is moved dynamically along a predetermined path according to parameters said in the computer program.

In a preferred embodiment projection means is adapted to project an illuminated target onto a screen positioned symmetrically with regard to the primary position.

U.S. Pat. No. 5,094,521 also reveals a method of ocular testing comprising the steps of:
a) detecting the visual axis of at least one eye of the patient instructed to look at a target,
b) computing the position of said visual axis with reference to a primary position,
c) storing the position of the text and the visual axis, and
d) repeating steps (a–c) for different target positions thereby to derive ocular motility data.

The present invention is characterised in that said detecting step (a) comprises detection of the visual axes of both eyes of a patient instructed to look at a target by left and right gaze-detecting means positioned adjacent the patient. The target may be projected onto a screen symmetrically relative to said primary position, and wherein the target is projected from a position above the head of the patient. Step (a) may further comprise the simultaneous detection of the visual axis of both eyes of a patient instructed to look at the target. In a preferred form of the invention the visual axis of one eye of the patient is occluded during the testing procedure. The target may be moved in a series of preprogrammed steps, or may move dynamically along a predetermined path.

An embodiment of the present invention will now be described, by way of example, with reference to the accompanying drawing which is a diagrammatic representation partly in plan view of a system with apparatus for use in ocular motility testing in accordance with the present invention.

Ocular motility testing in the context of the present invention is concerned with the degree of accuracy or error in the direction of gaze of each eye of an observer instructed to look at a target displayed successively at different positions on a screen. Although such testing involves movements of the eyes to re-direct the gaze directions towards the different target positions, it should be understood that ocular motility test data consists essentially of static measurements for each specific target position. The present ocular motility testing is not concerned with dynamic measurements during eye movements. However, it is envisaged that ocular motility testing can feature a continuously moving target provided that the speed of movement is not too fast to prevent the obtaining of effective static measurements for different specific target positions.

In the drawing, the system apparatus features display means in the form a projector 10 adapted to project a target 11, being a spot of light, onto screen 12 which is positioned symmetrically with respect to a centre line 13 (primary position—looking straight ahead). An observer 14 is positioned immediately below the projector 10 and on the centre line 13. The screen 12 may be curved or flat; but a screen curved to a radius equal to the observer/screen distance simplifies computation of positions as will become apparent herebelow.

The projector 10 is adapted to be capable of projecting the target 11 to any specific position on the screen 12 in response to signals issued by a control console 15 which provides an operator with the choice of moving the target according to a predetermined program and/or selectively to successive different positions.

The system apparatus further includes detecting means 16 disposed close to the eyes of the observer 14 and on the respective visual axes thereof. The detecting means 16 features mutually independent left and right gaze-direction detectors 25 and occluders 23. Each gaze-direction detector uses beam splitters 24 and known video technology to detect eyeball movement and to produce signals which can be interpreted to provide data representing the direction of the visual axis with reference to the primary position or centre line 13, using polar, co-ordinate or other angular measurements. Thus, a computing means 17 is adapted to calculate independently the visual axis directions for left and right eyes.

In this description and in the appended claims, the term "position" is a reference to any kind or format of data which defines, with reference to the centre line 13 and/or its intersection with the screen 12, the direction of gaze or the direction of the target from the eye.

The occluders 23 incorporated in the detecting means 16 are operable simply to occlude sight of the target from one or other eye according to choice of the operator or the program.

Outputs from the computing means 17 are fed to further computing means 18 adapted to calculate, using either polar or co-ordinate values, the positions of the left and right visual axes with reference to the primary position, and these positions are in turn fed to a store means 19. The position of the target 11 is passed directly to the store means 19 from the control console 15. It will be understood that the store means 19 is capable of storing successive different positions of the target 11.

A comparator means 20 is linked with outputs from the store means 19 and is operable in response to the control console 15 to process all of the stored positions to provide correlation information in a form suitable for displaying and/or printing respectively on a visual display unit 21 or printer 22.

In operation of the system apparatus above described, the observer 14 is simply instructed to look at the target 11 which is moved to successive different positions either step-wise or dynamically according to a program or according to the choice of the operator. Without further instruction to the observer 14 and without any other action required from the observer, the gaze directions for each eye, or for either eye, are detected and converted to position data and stored in the store means 19 together with the corresponding data for each of the target positions. If testing is done on a dynamic basis, it will be understood that a sampling time element will be introduced.

Subsequently, under the control of the operator, the stored position data is read out from the store means 19 and processed by means of the comparator 20 for display and/or printing.

In a modification of the system apparatus as described above, the left, right and target position data may effectively be stored directly by means of the visual display unit 21 and/or printer 22, thus by-passing the store means 19 and/or comparator 20. In the foregoing description and in the appended claims, the term "store" and its related terms embraces any medium for keeping a record of multiple data items. In another modification, the screen/projector arrangement is replaced by a video display unit which can be driven in known manner to emulate the screen/projector function. These modifications are within the scope of the appended claims.

I claim:

1. An apparatus for ocular motility testing comprising, head positioning means for location of the head of a patient in a predetermined position, gaze-detecting means adapted to image both eyes simultaneously with the patient's head in a predetermined position while the patient's eye(s) follow a target on a screen, and computing means for computing the position of visual axis of said eyes with reference to a primary position, and store means associated with a target display means and said computing means to store the positions of the target and the positions of the visual axes;

characterized in that the gaze-detecting means is disposed adjacent the eyes of the patient and comprises left and right gaze direction detecting means acting independently, the gaze-detecting means including gaze occluder means operable selectively to occlude a patient's eye relative to the target, without obstructing the gaze detecting means.

2. An apparatus according to claim 1 comprising projection means adapted to project an illuminated target onto a screen positioned symmetrically with regard to the primary position.

3. An apparatus according to claim 2 wherein the projection means is a video display unit.

4. An apparatus according to claim 2 including control means programmable to drive the projection means so that the target is either displayed at different positions or is moved dynamically along a predetermined path on the screen according to parameters set in a computer program.

5. A method of ocular testing comprising the steps of:

(a) detecting the visual axis of at least one eye of a patient instructed to look at the target, (b) computing the position of said visual axis with reference to a primary position, (c) storing the positions of the target and the visual axis, and (d) repeating steps (a–c) for several different target positions thereby to derive ocular motility data;

characterized in that said detecting step (a) comprises detection of the visual axes of both eyes of a patient instructed to look at a target, by left and right gaze-detecting means positioned adjacent the patient, the visual axis of one eye of a patient being selectively occluded from the target, without obstructing the gaze detecting means.

6. A method according to claim 5 wherein said target is projected on to a screen disposed substantially symmetrically relative to said primary position.

7. A method according to claim 5 wherein the target is moved in a series of preprogrammed steps, or moved dynamically along a predetermined path.

8. A method according to claim 6 wherein said target is projected onto a VDU screen.

* * * * *